(12) United States Patent
Uriu

(10) Patent No.: US 11,913,057 B2
(45) Date of Patent: *Feb. 27, 2024

(54) METHOD FOR DETERMINING WHETHER OR NOT TEST SAMPLE CONTAINS PHYTOPATHOGENIC FUNGUS

(71) Applicant: Panasonic Intellectual Property Management Co., Ltd., Osaka (JP)

(72) Inventor: Yoshitsugu Uriu, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 221 days.

This patent is subject to a terminal disclaimer.

(21) Appl. No.: 17/498,391

(22) Filed: Oct. 11, 2021

(65) Prior Publication Data

US 2022/0025427 A1  Jan. 27, 2022

Related U.S. Application Data

(60) Division of application No. 16/410,362, filed on May 13, 2019, now Pat. No. 11,168,346, which is a continuation of application No. PCT/JP2017/008407, filed on Mar. 3, 2017.

(30) Foreign Application Priority Data

Jan. 25, 2017  (JP) .................. 2017-010913

(51) Int. Cl.
*C12Q 1/04* (2006.01)
*C12M 1/34* (2006.01)
*C12M 1/00* (2006.01)

(52) U.S. Cl.
CPC .............. *C12Q 1/04* (2013.01); *C12M 1/34* (2013.01); *C12M 23/20* (2013.01)

(58) Field of Classification Search
None
See application file for complete search history.

(56) References Cited

U.S. PATENT DOCUMENTS

| 9,410,210 B2 | 8/2016 | Mach et al. |
| 2018/0208960 A1 | 7/2018 | Yamaguchi et al. |

FOREIGN PATENT DOCUMENTS

| EP | 1400366 A2 | 3/2004 |
| EP | 3301172 A1 | 4/2018 |
| EP | 3438277 A1 | 2/2019 |
| EP | 3498858 A1 | 6/2019 |
| JP | 2005-287337 A | 10/2005 |

OTHER PUBLICATIONS

Millipore; "Cell Culture Solutions: Millicell® Inserts & Sterile Filtration" product selection guide; Millipore Corporation: Billerica, MA; pp. 1-16). (Year: 2008).*
Cao et al, "Structure and properties of cellulose films coated with polyurethane/benzyl starch semi-IPN coating" Ind. Eng. Chem. Res. (2006) 45, 4193-4199 (Year: 2006).
Zhang et al "Molecular detection of *Fusarium oxysporum* f. sp. *niveum* and *Mycosphaerella melonis* in infected plant issues and soil," FEMS Microbiology Letters 249 (2005) 39-47 (Year: 2005).
International Search Report of PCT application No. PCT/JP2017/008407 dated Jun. 6, 2017.
Paul F. Morris et al., "Chemotropic and Contact Responses of Phytophthora sojae Hyphae to Soybean Isoflavonoids and Artificial Substrates", Plant Physiol. (1998) 117: 1171-1178, Aug. 1998.
The Extended European Search Report dated Feb. 11, 2020 for the related European Patent Application No. 17893638.1.
Non-Frinal Office Action issued in U.S. Appl. No. 16/410,362, dated Dec. 8, 2020.
Notice of Allowance issued in U.S. Appl. No. 16/410,362, dated Jul. 14, 2021.

\* cited by examiner

*Primary Examiner* — Michelle F. Paguio Frising
(74) *Attorney, Agent, or Firm* — Rimon P.C.

(57) ABSTRACT

A method for determining whether a test sample contains a phytopathogenic fungus selectively from two kinds of fungi of a phytopathogenic fungus and a non-phytopathogenic fungus. The method comprises: (a) putting the test sample on a front surface of a substrate comprising a through hole; wherein the substrate comprises a cellulose film on a back surface thereof; the cellulose film has no through hole; the cellulose film has a thickness of more than 2 micrometers and not more than 3.7 micrometers; and the through hole has a cross-sectional area of not less than 7.065 square micrometers and not more than 19.625 square micrometers; (b) leaving the test sample at rest; (c) observing a back surface of the cellulose film; and (d) determining that the test sample contains the phytopathogenic fungus, if a fungus which has penetrated the cellulose film is found on the back surface of the cellulose film.

1 Claim, 7 Drawing Sheets

METHOD FOR DETERMINING WHETHER OR NOT TEST SAMPLE CONTAINS PHYTOPATHOGENIC FUNGUS

CROSS-REFERENCE OF RELATED APPLICATIONS

This application is a Divisional application of U.S. patent application Ser. No. 16/410,362, filed on May 13, 2019, which is a Continuation of International Patent Application No. PCT/JP2017/008407, filed on Mar. 3, 2017, which in turn claims the benefit of Japanese Application No. 2017-010913, filed on Jan. 25, 2017, the entire disclosures of which applications are incorporated by reference herein.

BACKGROUND

1. Technical Field

The present invention relates to a method for determining whether or not a test sample contains a phytopathogenic fungus.

2. Description of the Related Art

Patent Literature 1 discloses a method for counting the number of mold cells in a specimen by the culture for a short time and capable of accurately counting the cell number. FIG. 10 shows a cross-sectional view of a microporous membrane supporting material used for the method disclosed therein. According to this method, the extended multiple pseudomycelia of a mold cell 13 cultured by a liquid culture or a mold cell 13 cultured on a microporous membrane 1 of a microporous membrane supporting material 4 are photographed and the shape, area and luminous intensity are recognized and analyzed by an image analytic means 10. The number of the mold cells 13 can be counted by the culture for a short time. The microporous membrane 1 is interposed between a pressing ring 2 and a base 3.

Non-patent Literature 1 discloses that hyphae of *Phytophthora sojae*, which is one of phytopathogenic oomycetes, penetrates the PET membrane having 3-micrometer pores.

CITATION LIST

Patent Literature

Patent Literature 1: Japanese Patent Application Publication No. 2005-287337

Non-Patent Literature

Non-patent Literature 1: Paul F. Morris. et. al. "Chemotropic and Contact Responses of *Phytophthora sojae* Hyphae to Soybean Isoflavonoids and Artificial Substrates", Plant Physiol. (1998) 117: 1171-1178

SUMMARY

Technical Problem

An object of the present invention is to provide a method for selectively determining whether or not a test sample contains a phytopathogenic fungus selectively from two kinds of fungi of a phytopathogenic fungus and a non-phytopathogenic fungus.

Solution to Problem

The present invention provides a method for determining whether or not a test sample contains a phytopathogenic fungus, the method comprising:
(a) putting the test sample on a front surface of a substrate comprising a through hole;
wherein
the substrate comprises a cellulose film on a back surface thereof;
the cellulose film has no through hole;
the cellulose film has a thickness of more than 2 micrometers and not more than 3.72 micrometers; and
the through hole has a cross-sectional area of not less than 7.065 square micrometers and not more than 19.625 square micrometers;
(b) leaving the test sample at rest after the step (a);
(c) observing a back surface of the cellulose film after the step (b); and
(d) determining that the test sample contains the phytopathogenic fungus, if a fungus which has penetrated the cellulose film is found on the back surface of the film in the step (c).

Advantageous Effects of Invention

The present invention provides a method for selectively determining whether or not a test sample contains a phytopathogenic fungus selectively from two kinds of fungi of a phytopathogenic fungus and a non-phytopathogenic fungus.

DETAILED DESCRIPTION OF THE EMBODIMENT

Figure 1:
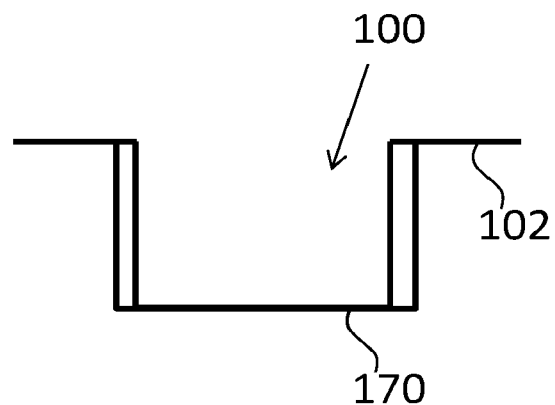
FIG. 1 shows a cross-sectional view of a first container 100.

First, a fungus will be described. Fungi are roughly divided into a phytopathogenic fungus and a non-phytopathogenic fungus. For example, the phytopathogenic fungus is a *Fusarium* genus, a *Pyricularia* genus, or a

*Colletotrichum* genus. An example of the phytopathogenic fungus is *Fusarium oxysporum, Pyricularia grisea*, or *Colletotrichum gloeosporioides*. These phytopathogenic fungi cause root rot disease, blast, anthrax, or gray mold. These phytopathogenic fungi kill the plant. An example of the non-phytopathogenic fungus is *Saccharomyces cerevisiae, Penicillium chysogeum* or *Aspergillus oryzae*.

The term "phytopathogenic" means to have pathogenicity to plants. The term "non-phytopathogenic" means not to have pathogenicity to plants. Even if a fungus has pathogenicity, however, if the fungus has no pathogenicity to plants, the fungus is non-phytopathogenic. In other words, if a fungus does not have adverse effects on plants, the fungus is non-phytopathogenic. The prefix "non-" included in the term "non-phytopathogenic" does not modify "phyto". The prefix "non-" modifies "pathogenic".

Hereinafter, the embodiment of the present invention will be described in more detail with reference to the drawings.

(Step (a))

In the step (a), a test sample is put on a front surface of a substrate 170 comprising through holes 172. A cellulose film 104 is adhered to a back surface 170b of the substrate 170. In other words, a front surface 104a of the cellulose film 104 is in contact with the back surface 170b of the substrate 170.

In particular, as shown in FIG. 1, a container 100 is prepared. It is desirable that the container 100 comprises a flange 102 at the upper end thereof. The bottom surface of the container 100 is formed of the substrate 170.

Figure 2:
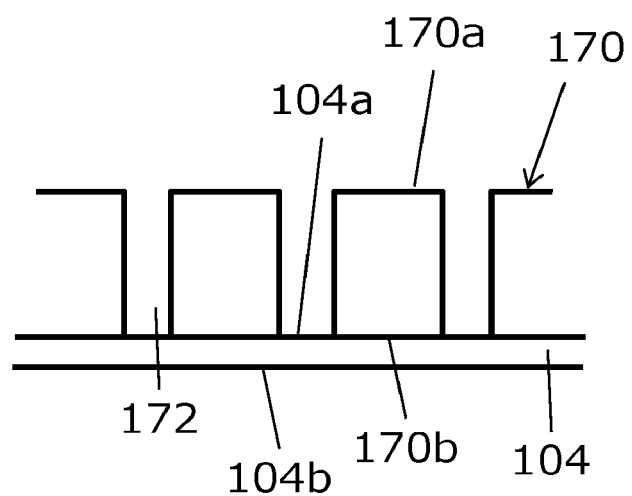
FIG. 2 shows a cross-sectional view of a substrate 170 comprising a cellulose film 104 on the back surface thereof.

As shown in FIG. 2, the substrate 170 comprises the cellulose film 104 on the back surface 170b thereof. The substrate 170 comprises a through hole 172 which penetrates from the front surface 170a to the back surface 170b of the substrate 170. The through hole 172 has a diameter of not less than 3 micrometers and not more than 5 micrometers. In other words, the through hole 172 has a cross-sectional diameter of not less than 7.065 square micrometers and not more than 19.625 square micrometers. Unlike the substrate 170, note that the cellulose film 104 has no through hole.

Figure 3:
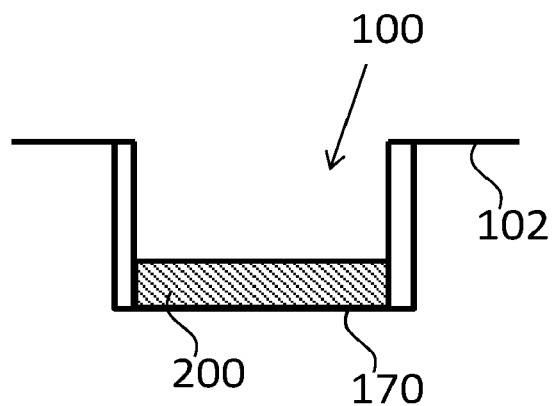
FIG. 3 shows a cross-sectional view of the first container 100 to which a test sample has been supplied.
Figure 4:
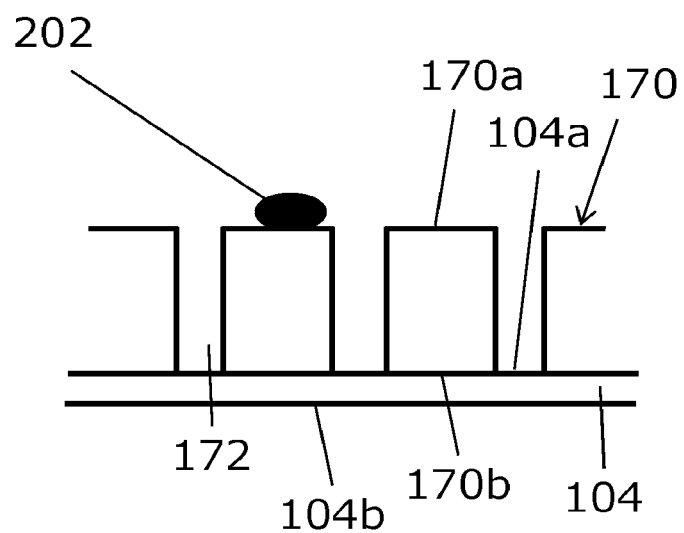
FIG. 4 shows a cross-sectional view of the substrate 170 having a front surface on which a phytopathogenic fungus has been put.

As shown in FIG. 3, a test sample 200 is supplied to the inside of this container 100. In this way, the test sample 200 is put on the front surface 170a of the substrate 170. When the test sample 200 contains a phytopathogenic fungus 202, the phytopathogenic fungus 202 is put on the front surface 170a of the substrate 170, as shown in FIG. 4.

The test sample 200 is solid, liquid, or gaseous. It is desirable that the test sample 200 is solid or liquid. An example of the solid test sample 200 is soil or a crushed plant. Another example is an agricultural material such as vermiculite, rock wool or urethane. An example of the liquid test sample 200 is agricultural water, a solution used for hydroponic culture, a liquid used for washing a plant, a liquid extracted from a plant, a liquid used for washing an agricultural material, or a liquid used for washing clothing or shoes of a worker.

(Step (b))

In the step (b), the test sample 200 is left at rest for a certain incubation time after the step (a). Desirably, the test sample 200 is left at rest for 24 hours. In this way, the fungus is incubated. In other words, the incubation time is approximately 24 hours. Hereinafter, the importance of the thickness of the cellulose film 104 and the size of the through hole 172 will be described.

Figure 5:
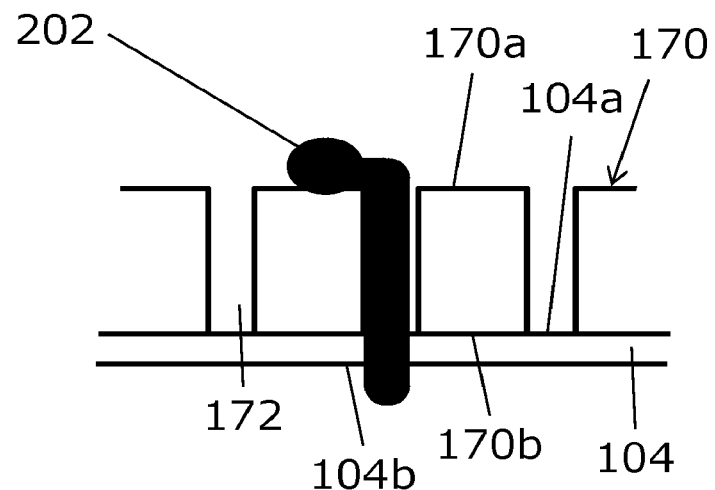
FIG. 5 is a cross-sectional view showing a state where the phytopathogenic fungus has penetrated a through-hole 172 and the cellulose film 104.

In the step (b), various fungi contained in the test sample 200 are grown. As demonstrated in the experiments which will be described later, if both of the following requirements (I) and (II) are satisfied, the phytopathogenic fungus 202 grows up so as to penetrate both the through hole 172 and the cellulose film 104, as shown in FIG. 5. As a result, the phytopathogenic fungus 202 appears on a back surface 104b of the cellulose film 104.

Requirement (I): The cellulose film 104 has a thickness of not less than 2 micrometers and not more than 3.7 micrometers.

Requirement (II): The through hole 172 has a cross-sectional diameter of not less than 7.065 square micrometers and not more than 19.625 square micrometers.

If both of the above requirements (I) and (II) are satisfied, the non-phytopathogenic fungus hardly penetrates the cellulose film 104. As demonstrated in the comparative example 6D, at a maximum, the number of hyphae which penetrated cellulose film 104 is 2.7. For this reason, the non-phytopathogenic fungus hardly appears on the back surface 104b of the cellulose film 104. On the other hand, the phytopathogenic fungus 202 appears on the back surface 104b selectively. As demonstrated in the inventive example 3D, at a minimum, the number of hyphae which penetrated cellulose film 104 is 7.0. As just described, the phytopathogenic fungus 202 appears outside of the container 100 selectively.

In case where the cellulose film 104 has a thickness of more than 4.4 micrometers, neither the non-phytopathogenic fungus nor the phytopathogenic fungus penetrates the cellulose film 104. Therefore, in case where the cellulose film 104 has a thickness of more than 4.4 micrometers, the selectivity is lost. When the cellulose film 104 has a thickness of less than 0.5 micrometers (including a case where the cellulose film 104 is not provided), not only the phytopathogenic fungus but also the non-phytopathogenic fungus penetrates the cellulose film 104 (or are found on the back surface 170b of the substrate 170). Therefore, the selectivity is lost when the cellulose film 104 has a thickness of less than 0.5 micrometers.

In case where the through hole 172 has a cross-sectional diameter of less than 7.065 square micrometers (namely, a diameter of less than 3 micrometers), neither the non-phytopathogenic fungus nor the phytopathogenic fungus penetrates the cellulose film 104. On the other hand, if the through hole 172 has a cross-sectional diameter of more than 19.625 square micrometers (namely, a diameter of more than 5 micrometers), the number of hyphae which penetrated cellulose film 104 tends to be lowered, compared to the case where the through hole 172 has a cross-sectional area of 19.625 square micrometers (namely, a diameter of 5 micrometers).

The cellulose film 104 is stretched taut on the back surface 170b of the substrate 170. As just described, the substrate 170 supports the cellulose film 104.

As shown in FIG. 2, it is desirable that the substrate 170 has a plurality of through holes 172. The thickness of the substrate 170 is not limited; however, as one example, it is desirable that the substrate 170 has a thickness of not less than 1 micrometer and not more than 500 micrometers. The cellulose film 104 is significantly thin. However, if the cellulose film 104 is arranged on the substrate 170, it is easy to handle the cellulose film 104.

A culture medium may be supplied to the test sample 200 to accelerate the incubation of the fungus. In particular, a culture medium may be supplied to the inside of the container 100 containing the test sample 200. It is desirable that the culture medium is liquid. The culture medium may be supplied in the step (b). Alternatively, the culture medium may be supplied prior to the step (b). In other words, the culture medium may be supplied in the step (a). The culture medium may be supplied to the inside of the container 100 prior to the step (a).

Figure 6:
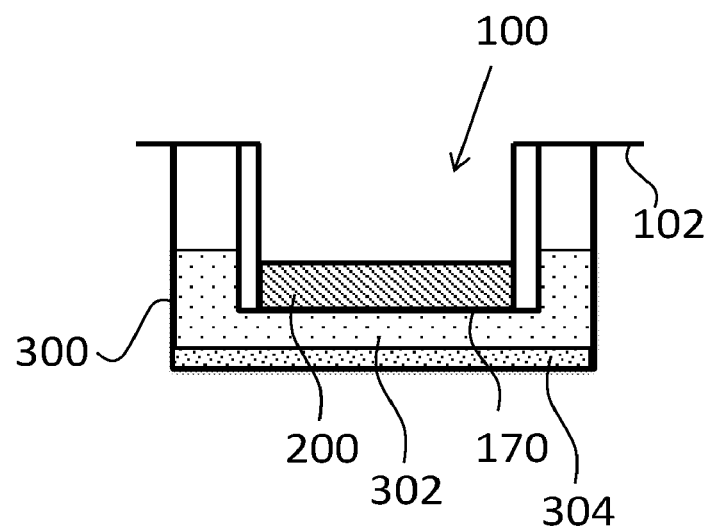
FIG. 6 shows a cross-sectional view of one example of a method for accelerating the incubation of the fungus.

FIG. 6 shows another method for accelerating the incubation of the fungus. As shown in FIG. 6, it is desirable that the back surface 104b of the cellulose film 104 is in contact with a liquid culture medium 302. First, a second container 300 having the liquid culture medium 302 therein is prepared. Hereinafter, the container 100 is referred to as "first container 100" to distinguish it from the second container 300. The first container 100 is stacked on the second container 300 in such a manner that the lower surface of the flange 102 is in contact with the upper end of the second container 300. In other words, the first container 100 is supported by the upper end of the second container 300. In this way, the liquid culture medium 302 is sandwiched between the back surface 104b of the cellulose film 104 and the bottom surface of the second container 300.

Alternatively, after the first container 100 is stacked on the second container 300, the liquid culture medium 302 may be supplied between the back surface 104b of the cellulose film 104 and the bottom surface of the second container 300.

In place of the liquid culture medium 302, a viscous solid culture medium may also be used. As shown in FIG. 6, both of a solid culture medium 304 and the liquid culture medium 302 may be used. In this case, the liquid culture medium 302 is sandwiched between the solid culture medium 304 and the cellulose film 104. As shown in FIG. 5, the incubation of the phytopathogenic fungus 202 which has appeared on the back surface 104b is accelerated by at least one of the liquid culture medium 302 and the solid culture medium 304.

(Step (c))

In the step (c), the back surface 104b of the cellulose film 104 is observed after the step (b). It is desirable that the back surface 104b is observed using an optical microscope.

The phytopathogenic fungus 202 appears on the back surface 104b of the cellulose film 104, as described in the step (b). On the other hand, the non-phytopathogenic fungus does not appear on the back surface 104b of the cellulose film 104. In this way, in the present invention, the phytopathogenic fungus 202 appears on the back surface 104b of the cellulose film 104 selectively.

In other words, the phytopathogenic fungus 202 penetrates the cellulose film 104, whereas the non-phytopathogenic fungus does not penetrate the cellulose film 104. For this reason, the non-phytopathogenic fungus does not appear on the back surface 104b of the cellulose film 104. In this way, the phytopathogenic fungus 202 appears on the back surface 104b selectively. In other words, the phytopathogenic fungus 202 appears outside of the first container 100 selectively.

In the step (c), it is observed whether or not the phytopathogenic fungus 202 appears on the back surface 104b of the cellulose film 104.

In particular, whether or not the phytopathogenic fungus 202 appears on the back surface 104b of the cellulose film 104 is observed as below.

Figure 8:
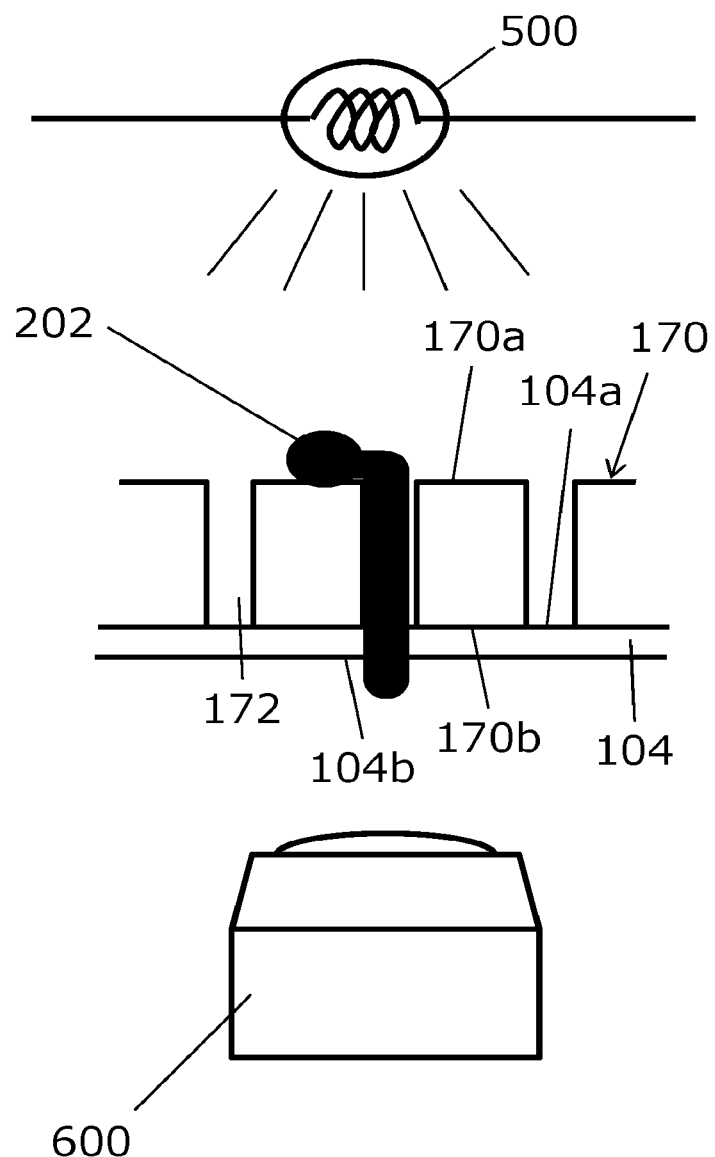
FIG. 8 is a cross-sectional view showing how to observe the fungus from the back surface of the cellulose film 104.

As shown in FIG. 8, while the cellulose film 104 is irradiated with light emitted from a light source 500 arranged above the front surface 170a of the substrate 170, the phytopathogenic fungus 202 is observed optically using a microscope 600 arranged below the back surface 104b of the cellulose film 104.

Figure 7:
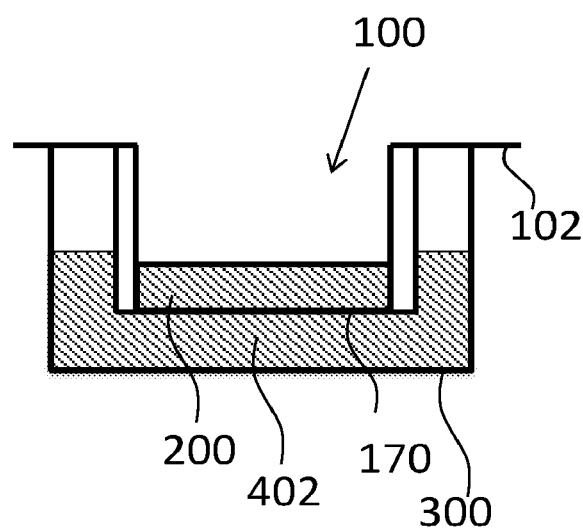
FIG. 7 shows a cross-sectional view, subsequently to FIG. 6, of one example of a method for accelerating the incubation of the fungus.

The liquid culture medium 302 and the solid culture medium 304 are removed from the second container 300. Then, a fungus fluorescent agent 402 is added to the inside of the second container 300. Then, as shown in FIG. 7, the first container 100 is stacked on the second container 300 having the fungus fluorescent agent 402 therein. Alternatively, the fungus fluorescent agent 402 may be supplied between the back surface 104b of the cellulose film 104 and the bottom surface of the second container 300 after the first container 100 is stacked on the second container 300.

A part of the phytopathogenic fungus 202 which has appeared on the back surface 104b of the cellulose film 104 may be dyed with the fungus fluorescent agent 402. Since the first container 100 is separated from the second container 300 by the cellulose film 104, the fungus fluorescent agent 402 does not spread into the first container 100. For this reason, the non-phytopathogenic fungus contained in the first container 100 is not dyed with the fungus fluorescent agent 402.

Figure 9:
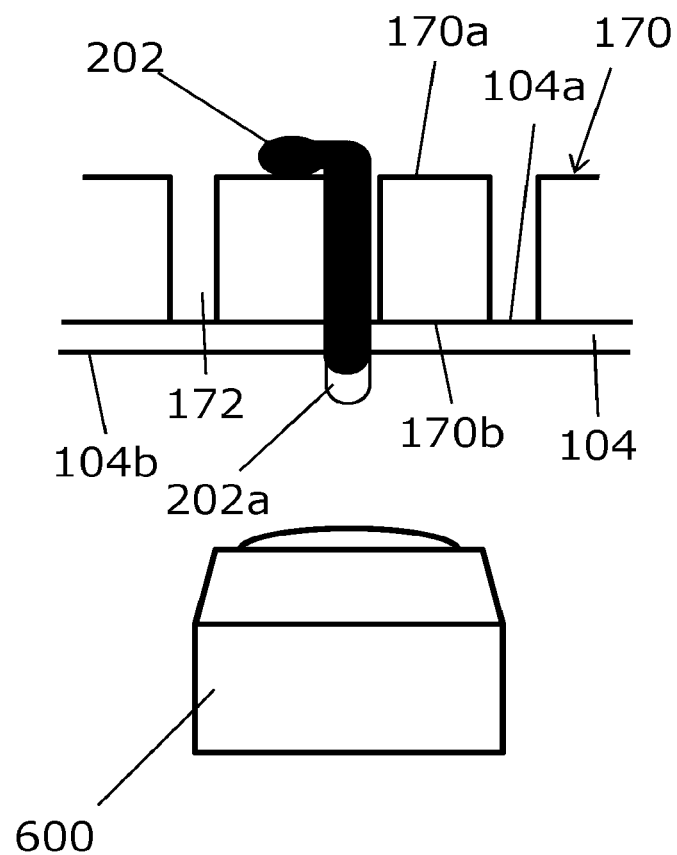
FIG. 9 is a cross-sectional view showing how to observe the fungus from the back surface of the cellulose film 104.
Figure 10:
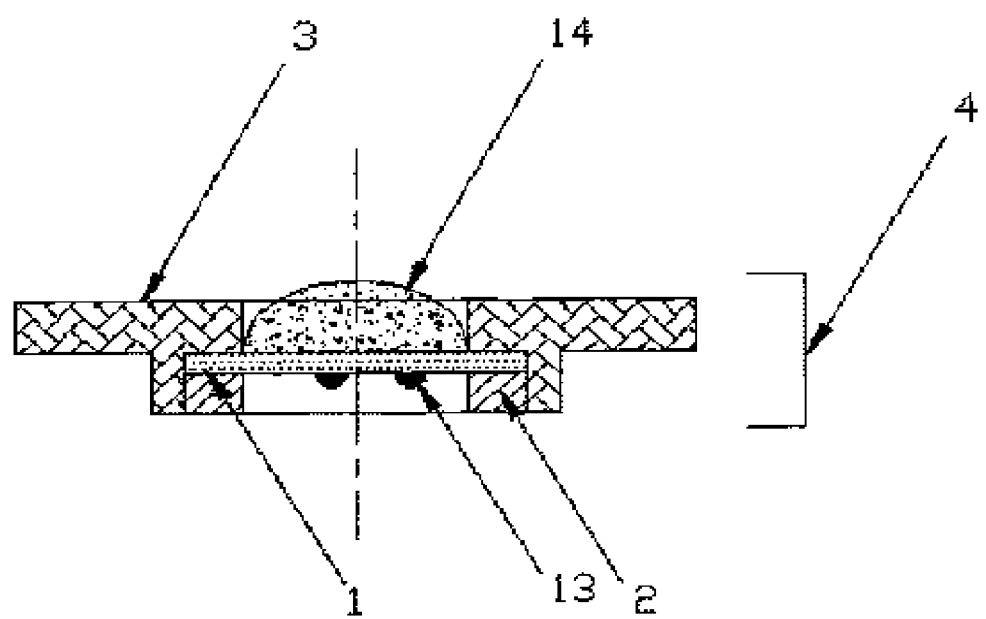
FIG. 10 shows a cross-sectional view of the microporous membrane supporting material used for the method for counting the number of mold cells disclosed in Patent Literature 1.

As shown in FIG. 9, the phytopathogenic fungus 202 dyed with the fungus fluorescent agent 402 is observed using the epifluorescence microscope 600 arranged under the back surface 104b of the cellulose film 104. Needless to say, the phytopathogenic fungus 202 may be observed without using the fungus fluorescent agent 402.

(Step (d))

In the step (d), it is determined that the test sample contains a phytopathogenic fungus, if a fungus is found on the back surface 104b of the cellulose film 104 in the step (c). Needless to say, it is determined that the test sample does not contain a phytopathogenic fungus, if a fungus is not found on the back surface 104b of the cellulose film 104 in the step (c).

EXAMPLES

The present invention will be described in more detail with reference to the following examples.

(Incubation of *Fusarium oxysporum*)

*Fusarium oxysporum*, one of phytopathogenic fungi, was inoculated on a potato dextrose agar culture medium. Then, the culture medium was left at rest at a temperature of 25 degrees Celsius for one week. *Fusarium oxysporum* was given by an associate professor, Mr. Shimizu, who belongs to Graduate School of Applied Biological Sciences and Faculty of Applied Biological Sciences, Gifu University.

Then, a part including ends of hyphae was cut together with the culture medium at a size of 1 centimeter×1 centimeter. The cut part was immersed in pure water disposed on a 12-well plate. Each of the pure water has a volume of 1 milliliter.

The water contained in the 12-well plate was observed using an optical microscope. As a result, the present inventors confirmed that spores of *Fusarium oxysporum* were released in the water disposed on the 12-well plate. In this way, an aqueous solution containing *Fusarium oxysporum* was provided. Hereinafter, this aqueous solution is referred to as "phytopathogenic fungus aqueous solution".

(Preparation of Culture Medium)

A potato dextrose culture medium having a volume of 650 microliters was added as the liquid culture medium 302 to the second container 300. In this way, the second container 300 containing the liquid culture medium 302 was prepared.

Experiment 1

The experiment 1 is composed of inventive examples 1A-1D, referential examples 1E-1F, and comparative examples 1G-1T.

Inventive Example 1A

The first container 100 shown in FIG. 1 was prepared as below.

First, cellulose (available from SIGMA-ALDRICH Co. LLC, trade name: Avicel PH-101) was dissolved in an ionic liquid to prepare a cellulose solution having a concentration of 2%. The ionic liquid was 1-butyl-3-methyl imidazolium chloride (available from SIGMA-ALDRICH Co. LLC).

The cellulose solution was warmed to 60 degrees Celsius. Then, the cellulose solution was applied by a spin coat method for thirty seconds at a rotation speed of 2,000 rpm onto a back surface of a container having a polyethylene terephthalate film on the bottom surface thereof (available from Merck KGaA, trade name: Millicell PISP 12R 48). The polyethylene terephthalate film served as the substrate 170. The polyethylene terephthalate film randomly had a plurality of through holes 172 each having a diameter of three micrometers. In this way, the cellulose film 104 having a thickness of 2.0 micrometers was formed on the back surface of the polyethylene terephthalate film. According to Merck KGaA, the diameter of the through-hole 172 may have a margin of error of approximately ±10%.

The container was left at rest in ethanol at room temperature for 12 hours. In this way, 1-butyl-3-methyl imidazolium chloride was replaced with ethanol. In other words, 1-butyl-3-methyl imidazolium chloride was removed from the cellulose film 104.

Finally, the container was dried in a vacuum desiccator. In this way, the first container 100 shown in FIG. 1 was obtained. In FIG. 1, note that the polyethylene terephthalate film serving as the substrate 170 is not illustrated.

Then, as shown in FIG. 6, the first container 100 was stacked on the second container 300. The back surface 104b of the cellulose film 104 was in contact with the liquid culture medium 302. Subsequently, water having a volume of 200 microliters was added to the inside of the first container 100. Furthermore, the phytopathogenic fungus aqueous solution containing 200 spores of *Fusarium oxysporum* was added to the inside of the first container 100.

The first container 100 was left at rest at a temperature of 25 degrees Celsius for 24 hours. In other words, in the inventive example 1A, the incubation time was 24 hours.

The number of the hyphae of *Fusarium oxysporum* which appeared on the back surface 104b of the cellulose film 104 was counted visually with an optical microscope. The inventive example 1A was repeated fifteen times. As a result, the mean value of the number of the hyphae of *Fusarium oxysporum* which appeared on the back surface 104b was 44.9.

Inventive Example 1B

In the inventive example 1B, an experiment similar to the inventive example 1A was conducted, except that each of the through holes 172 had a diameter of 5 micrometers. The container having a bottom surface comprising the through holes each having a diameter of 5 micrometers was available from Merck KGaA as a trade name: Millicell PIMP 12R 48.

Inventive Example 1C

In the inventive example 1C, an experiment similar to the inventive example 1A was conducted, except that the cellulose solution had a concentration of 3.0% and that the cellulose film 104 had a thickness of 3.7 micrometers.

Inventive Example 1D

In the inventive example 1D, an experiment similar to the inventive example 1A was conducted, except that the cellulose solution had a concentration of 3.0%, that the cellulose film 104 had a thickness of 3.7 micrometers, and that each of the through hole 172 had a dimeter of 5 micrometers.

Referential Example 1E

In the referential example 1E, an experiment similar to the inventive example 1A was conducted, except that the cellulose solution had a concentration of 1.0% and that the cellulose film 104 had a thickness of 0.5 micrometers.

Referential Example 1F

In the referential example 1F, an experiment similar to the inventive example 1A was conducted, except that (i) the cellulose solution had a concentration of 1.0%, that (ii) the cellulose film 104 had a thickness of 0.5 micrometers, and that (iii) the through hole 172 had a diameter of 5 micrometers.

Comparative Example 1G

In the comparative example 1G, an experiment similar to the inventive example 1A was conducted, except that the cellulose film 104 was not formed (namely, the cellulose film 104 had a thickness of 0 micrometers) and that the each of the through holes 172 had a diameter of 1 micrometer. The container having a bottom surface comprising through holes each having a diameter of 1 micrometer was available from Merck KGaA as a trade name: Millicell PIRP 12R 48.

Comparative Example 1H

In the comparative example 1H, an experiment similar to the inventive example 1A was conducted, except that the cellulose film 104 was not formed (namely, the cellulose film 104 had a thickness of 0 micrometers).

Comparative Example 1I

In the comparative example 1I, an experiment similar to the inventive example 1A was conducted, except that the cellulose film 104 was not formed (namely, the cellulose film 104 had a thickness of 0 micrometers) and that the each of the through holes 172 had a diameter of 5 micrometers.

Comparative Example 1J

In the comparative example 1J, an experiment similar to the inventive example 1A was conducted, except that the cellulose film 104 was not formed (namely, the cellulose film 104 had a thickness of 0 micrometers) and that the each of the through holes 172 had a diameter of 8 micrometers. The container having a bottom surface comprising through holes each having a diameter of 8 micrometers was available from Merck KGaA as a trade name: Millicell PIEP 12R 48.

Referential Comparative Example 1K

In the referential comparative example 1K, an experiment similar to the inventive example 1A was conducted, except that (i) the cellulose solution had a concentration of 1.0%, that (ii) the cellulose film 104 had a thickness of 0.5 micrometers, and that (iii) the through hole 172 had a diameter of 1 micrometer.

Referential Comparative Example 1L

In the referential comparative example 1L, an experiment similar to the inventive example 1A was conducted, except that (i) the cellulose solution had a concentration of 1.0%, that (ii) the cellulose film 104 had a thickness of 0.5 micrometers, and that (iii) the through hole 172 had a diameter of 8 micrometers.

Referential Comparative Example 1M

In the referential comparative example 1M, an experiment similar to the inventive example 1A was conducted, except that the through hole 172 had a diameter of 1 micrometer.

Referential Comparative Example 1N

In the referential comparative example 1N, an experiment similar to the inventive example 1A was conducted, except that the through hole 172 had a diameter of 8 micrometers.

Comparative Example 1O

In the comparative example 1O, an experiment similar to the inventive example 1A was conducted, except that (i) the cellulose solution had a concentration of 3.0%, that (ii) the cellulose film 104 had a thickness of 3.7 micrometers, and that (iii) the through hole 172 had a diameter of 1 micrometer.

Comparative Example 1P

In the comparative example 1P, an experiment similar to the inventive example 1A was conducted, except that (i) the cellulose solution had a concentration of 3.0%, that (ii) the cellulose film 104 had a thickness of 3.7 micrometers, and that (iii) the through hole 172 had a diameter of 8 micrometers.

Comparative Example 1Q

In the comparative example 1Q, an experiment similar to the inventive example 1A was conducted, except that (i) the cellulose solution had a concentration of 4.0%, that (ii) the cellulose film 104 had a thickness of 4.4 micrometers, and that (iii) the through hole 172 had a diameter of 1 micrometer.

Comparative Example 1R

In the comparative example 1R, an experiment similar to the inventive example 1A was conducted, except that the cellulose solution had a concentration of 4.0% and that the cellulose film 104 had a thickness of 4.4 micrometers.

Comparative Example 1S

In the comparative example 1S, an experiment similar to the inventive example 1A was conducted, except that (i) the cellulose solution had a concentration of 4.0%, that (ii) the cellulose film 104 had a thickness of 4.4 micrometers, and that (iii) the through hole 172 had a diameter of 5 micrometers.

Comparative Example 1T

In the comparative example 1T, an experiment similar to the inventive example 1A was conducted, except that (i) the cellulose solution had a concentration of 4.0%, that (ii) the cellulose film 104 had a thickness of 4.4 micrometers, and that (iii) the through hole 172 had a diameter of 8 micrometers.

Experiment 2

In the experiment 2, a non-phytopathogenic fungus aqueous solution containing spores of *Saccharomyces cerevisiae* was used in place of the phytopathogenic fungus aqueous solution containing spores of *Fusarium oxysporum*. Unlike *Fusarium oxysporum*, *Saccharomyces cerevisiae* is one kind of non-phytopathogenic fungus. A non-phytopathogenic fungus aqueous solution containing spores of *Saccharomyces cerevisiae* was prepared similarly to the case of the phytopathogenic fungus aqueous solution containing spores of *Fusarium oxysporum*. The experiment 2 is composed of comparative examples 2A-2T. The comparative examples 2A-2T were similar to the inventive example 1A-the comparative example 1T, except of using the different fungus.

Experiment 3

In the experiment 3, a phytopathogenic fungus aqueous solution containing spores of *Pyricularia grisea* was used in place of the phytopathogenic fungus aqueous solution containing spores of *Fusarium oxysporum*. Similarly to *Fusarium oxysporum*, *Pyricularia grisea* is one kind of phytopathogenic fungus. A phytopathogenic fungus aqueous solution containing spores of *Pyricularia grisea* was prepared as below.

(Incubation of *Pyricularia grisea*)

*Pyricularia grisea*, one of phytopathogenic fungi, was inoculated on an oatmeal agar culture medium containing 2% sucrose. Then, the culture medium was left at rest at a temperature of 25 degrees Celsius for one week. Subsequently, the culture medium was left at rest for four days under near-ultraviolet radiation.

Then, a part including ends of hyphae was cut together with the culture medium at a size of 1 centimeter×1 centimeter. The cut part was immersed in pure water disposed on a 12-well plate. Each of the pure water has a volume of 1 milliliter.

The water disposed on the 12-well plate was observed using an optical microscope. As a result, the present inventors confirmed that spores of *Pyricularia grisea* were released in the water disposed on the 12-well plate. In this way, an aqueous solution containing *Pyricularia grisea* was provided.

The experiment 3 is composed of the inventive examples 3A-3D, referential examples 3E-3F, and the comparative examples 3G-3T. The inventive examples 3A-3D, the referential examples 3E-3F, and the comparative examples 3G-3T were similar to the inventive examples 1A-1D, the referential examples 1E-1F, and the comparative examples 1G-1T, respectively, except of using the different fungus.

Experiment 4

In the experiment 4, a phytopathogenic fungus aqueous solution containing spores of *Colletotrichum gloeosporioides* was used in place of the phytopathogenic fungus aqueous solution containing spores of *Fusarium oxysporum*. Similarly to *Fusarium oxysporum*, *Colletotrichum gloeosporioides* is one kind of phytopathogenic fungus. A phytopathogenic fungus aqueous solution containing spores of *Colletotrichum gloeosporioides* was prepared similarly to the phytopathogenic fungus aqueous solution containing spores of *Fusarium oxysporum*. The experiment 4 is composed of inventive examples 4A-4D, the referential examples 4E-4F, and the comparative examples 4G-4T. The inventive examples 4A-4D, the referential examples 4E-4F, and the comparative examples 4G-4T were similar to the inventive examples 1A-1D, the referential examples 1E-1F, and the comparative examples 1G-1T, respectively, except of using the different fungus.

Experiment 5

In the experiment 5, a non-phytopathogenic fungus aqueous solution containing spores of *Penicillium chysogeum* was used in place of the phytopathogenic fungus aqueous solution containing spores of *Fusarium oxysporum*. Unlike *Fusarium oxysporum*, *Penicillium chysogeum* is one kind of non-phytopathogenic fungus. A non-phytopathogenic fungus aqueous solution containing spores of *Penicillium chysogeum* was prepared similarly to the case of the phytopathogenic fungus aqueous solution containing spores of *Fusarium oxysporum*. The experiment 5 is composed of comparative examples 5A-5T. The comparative examples 5A-5T were similar to the inventive example 1A-the comparative example 1T, except of using the different fungus.

Experiment 6

In the experiment 6, a non-phytopathogenic fungus aqueous solution containing spores of *Aspergillus oryzae* was used in place of the phytopathogenic fungus aqueous solution containing spores of *Fusarium oxysporum*. Unlike *Fusarium oxysporum*, *Aspergillus oryzae* is one kind of non-phytopathogenic fungus. A non-phytopathogenic fungus aqueous solution containing spores of *Aspergillus oryzae* was prepared similarly to the case of the phytopathogenic fungus aqueous solution containing spores of *Fusarium oxysporum*. The experiment 6 is composed of comparative examples 6A-6T. The comparative examples 6A-6T were similar to the inventive example 1A-the comparative example 1T, except of using the different fungus.

The following Table 1-Table 6 show the number of the hyphae which penetrated the cellulose film 104 in the experiments.

TABLE 1

| | film thickness (μm) | Diameter of Through hole (μm) | Name of Fungus | Number of hyphae which penetrated cellulose film 104 |
|---|---|---|---|---|
| C. Example 1G | 0 | 1 | *Fusarium oxysporum* (phytopathogenic) | 0.3 |
| C. Example 1H | | 3 | | 125.3 |
| C. Example 1I | | 5 | | 33.3 |
| C. Example 1J | | 8 | | 15 |
| R. C. Example 1K | 0.5 | 1 | | 0.5 |
| R. Example 1E | | 3 | | 106.5 |
| R. Example 1F | | 5 | | 94.1 |
| R. C. Example 1L | | 8 | | 125.4 |
| R. C. Example 1M | 2 | 1 | | 0 |
| I. Example 1A | | 3 | | 44.9 |
| I. Example 1B | | 5 | | 42.8 |
| R. C. Example 1N | | 8 | | 16.3 |
| C. Example 1O | 3.7 | 1 | | 0 |
| I. Example 1C | | 3 | | 40.0 |
| I. Example 1D | | 5 | | 12.0 |
| C. Example 1P | | 8 | | 8.0 |
| C. Example 1Q | 4.4 | 1 | | 0 |
| C. Example 1R | | 3 | | 0 |

TABLE 1-continued

| | film thickness (μm) | Diameter of Through hole (μm) | Name of Fungus | Number of hyphae which penetrated cellulose film 104 |
|---|---|---|---|---|
| C. Example 1S | | 5 | | 0 |
| C. Example 1T | | 8 | | 0 |

Incubation time: 24 hours
I. Inventive
R. Referential
C. Comparative

TABLE 2

| | film thickness (μm) | Diameter of Through hole (μm) | Name of Fungus | Number of hyphae which penetrated cellulose film 104 |
|---|---|---|---|---|
| C. Example 2G | 0 | 1 | *Saccharomyces cerevisiae* (non-phytopathogenic) | 0 |
| C. Example 2H | | 3 | | 0 |
| C. Example 2I | | 5 | | 0 |
| C. Example 2J | | 8 | | 0 |
| C. Example 2K | 0.5 | 1 | | 0 |
| C. Example 2E | | 3 | | 0 |
| C. Example 2F | | 5 | | 0 |
| C. Example 2L | | 8 | | 0 |
| C. Example 2M | 2 | 1 | | 0 |
| C. Example 2A | | 3 | | 0 |
| C. Example 2B | | 5 | | 0 |
| C. Example 2N | | 8 | | 0 |
| C. Example 2O | 3.7 | 1 | | 0 |
| C. Example 2C | | 3 | | 0 |
| C. Example 2D | | 5 | | 0 |
| C. Example 2P | | 8 | | 0 |
| C. Example 2Q | 4.4 | 1 | | 0 |
| C. Example 2R | | 3 | | 0 |
| C. Example 2S | | 5 | | 0 |
| C. Example 2T | | 8 | | 0 |

Incubation time: 24 hours
C. Comparative

TABLE 3

| | film thickness (μm) | Diameter of Through hole (μm) | Name of Fungus | Number of hyphae which penetrated cellulose film 104 |
|---|---|---|---|---|
| C. Example 3G | 0 | 1 | *Pyricularia grisea* (phytopathogenic) | 4 |
| C. Example 3H | | 3 | | 11 |
| C. Example 3I | | 5 | | 15.7 |
| C. Example 3J | | 8 | | 7.7 |
| R. C. Example 3K | 0.5 | 1 | | 8 |
| R. Example 3E | | 3 | | 85.3 |
| R. Example 3F | | 5 | | 77.4 |
| R. C. Example 3L | | 8 | | 99.4 |
| R. C. Example 3M | 2 | 1 | | 2 |
| I. Example 3A | | 3 | | 64.1 |
| I. Example 3B | | 5 | | 53 |
| R. C. Example 3N | | 8 | | 84.9 |
| C. Example 3O | 3.7 | 1 | | 0 |
| I. Example 3C | | 3 | | 6.5 |
| I. Example 3D | | 5 | | 7.0 |
| C. Example 3P | | 8 | | 7.0 |
| C. Example 3Q | 4.4 | 1 | | 0 |
| C. Example 3R | | 3 | | 7.0 |

TABLE 3-continued

| | film thickness (μm) | Diameter of Through hole (μm) | Name of Fungus | Number of hyphae which penetrated cellulose film 104 |
|---|---|---|---|---|
| C. Example 3S | | 5 | | 11.5 |
| C. Example 3T | | 8 | | 1 |

Incubation time: 24 hours
I. Inventive
R. Referential
C. Comparative

TABLE 4

| | film thickness (μm) | Diameter of Through hole (μm) | Name of Fungus | Number of hyphae which penetrated cellulose film 104 |
|---|---|---|---|---|
| C. Example 4G | 0 | 1 | *Colletotrichum* | 1.3 |
| C. Example 4H | | 3 | *gloeosporioides* | 182.7 |
| C. Example 4I | | 5 | (phytopathogenic) | 91.3 |
| C. Example 4J | | 8 | | 62.7 |
| R. C. Example 4K | 0.5 | 1 | | 4 |
| R. Example 4E | | 3 | | 326 |
| R. Example 4F | | 5 | | 449 |
| R. C. Example 4L | | 8 | | 165.3 |
| R. C. Example 4M | 2 | 1 | | 0 |
| I. Example 4A | | 3 | | 83.3 |
| I. Example 4B | | 5 | | 55.2 |
| R. C. Example 4N | | 8 | | 8.7 |
| C. Example 4O | 3.7 | 1 | | 0 |
| I. Example 4C | | 3 | | 22.0 |
| I. Example 4D | | 5 | | 10.0 |
| C. Example 4P | | 8 | | 2.5 |
| C. Example 4Q | 4.4 | 1 | | 0 |
| C. Example 4R | | 3 | | 0 |
| C. Example 4S | | 5 | | 0 |
| C. Example 4T | | 8 | | 0 |

Incubation time: 24 hours
I. Inventive
R. Referential
C. Comparative

TABLE 5

| | film thickness (μm) | Diameter of Through hole (μm) | Name of Fungus | Number of hyphae which penetrated cellulose film 104 |
|---|---|---|---|---|
| C. Example 5G | 0 | 1 | *Penicillium* | 0 |
| C. Example 5H | | 3 | *chysogeum* | 0 |
| C. Example 5I | | 5 | (non- | 0 |
| C. Example 5J | | 8 | phytopathogenic) | 0 |
| C. Example 5K | 0.5 | 1 | | 0 |
| C. Example 5E | | 3 | | 0 |
| C. Example 5F | | 5 | | 0 |
| C. Example 5L | | 8 | | 0 |
| C. Example 5M | 2 | 1 | | 0 |
| C. Example 5A | | 3 | | 0 |
| C. Example 5B | | 5 | | 0 |
| C. Example 5N | | 8 | | 0 |
| C. Example 5O | 3.7 | 1 | | 0 |
| C. Example 5C | | 3 | | 0 |
| C. Example 5D | | 5 | | 0 |
| C. Example 5P | | 8 | | 0 |
| C. Example 5Q | 4.4 | 1 | | 0 |
| C. Example 5R | | 3 | | 0 |
| C. Example 5S | | 5 | | 0 |
| C. Example 5T | | 8 | | 0 |

Incubation time: 24 hours
C. Comparative

TABLE 6

| | film thickness (μm) | Diameter of Through hole (μm) | Name of Fungus | Number of hyphae which penetrated cellulose film 104 |
|---|---|---|---|---|
| C. Example 6G | 0 | 1 | *Aspergillus oryzae* | 1 |
| C. Example 6H | | 3 | (non- | 48 |
| C. Example 6I | | 5 | phytopathogenic) | 56 |
| C. Example 6J | | 8 | | 23.7 |
| C. Example 6K | 0.5 | 1 | | 1 |
| C. Example 6E | | 3 | | 31.9 |
| C. Example 6F | | 5 | | 18.8 |
| C. Example 6L | | 8 | | 18.9 |
| C. Example 6M | 2 | 1 | | 0 |
| C. Example 6A | | 3 | | 0 |
| C. Example 6B | | 5 | | 2.7 |
| C. Example 6N | | 8 | | 1.6 |
| C. Example 6O | 3.7 | 1 | | 0 |
| C. Example 6C | | 3 | | 0 |
| C. Example 6D | | 5 | | 0 |
| C. Example 6P | | 8 | | 0 |
| C. Example 6Q | 4.4 | 1 | | 0 |
| C. Example 6R | | 3 | | 0 |
| C. Example 6S | | 5 | | 0 |
| C. Example 6T | | 8 | | 0 |

Incubation time: 24 hours
C. Comparative

As is clear from Table 1-Table 6, when both of the following requirements (I) and (II) are satisfied, the phytopathogenic fungus appears on the back surface 104b of the cellulose film 104 selectively. In other words, the phytopathogenic fungus 202 appears outside of the container 100 selectively.

Requirement (I): The cellulose film 104 has a thickness of not less than 2 micrometers and not more than 3.7 micrometers.

Requirement (II): The through hole 172 has a diameter of not less than 3 micrometers and not more than 5 micrometers.

As demonstrated in the inventive example 3D in which both of the requirements (I) and (II) are satisfied, the number of hyphae which penetrated cellulose film 104 is 7.0 at a minimum. On the other hand, as long as both of the requirements (I) and (II) are satisfied, the non-phytopathogenic fungus hardly appears on the back surface 104b the cellulose film 104. As demonstrated in the comparative example 6D in which both of the requirements (I) and (II) are satisfied, the number of hyphae which penetrated cellulose film 104 is 2.7 at a maximum.

INDUSTRIAL APPLICABILITY

The present invention can be used to determine easily whether or not a test sample such as agricultural water, a crushed plant or soil contains a phytopathogenic fungus.

REFERENCE SIGNS LIST

100 First container
102 Flange
104 Cellulose film
104*a* Front surface
104*b* Back surface
170 Substrate
170*a* Front surface
170*b* Back surface
200 Test sample
202 Phytopathogenic fungus
202*a* Part of Phytopathogenic fungus
300 Second container
302 Liquid culture medium
304 Solid culture medium
402 fungus fluorescent agent
500 Light source
600 Microscope

The invention claimed is:

1. A container having a bottom part, wherein
the bottom part is formed of a substrate;
a cellulose film is adhered on an outside surface of the bottom part;
the cellulose film has a thickness of more than 2 micrometers and not more than 3.7 micrometers;
the substrate comprises a through hole;
the cellulose film has no through hole; and
the through hole has a cross-sectional area of not less than 7.065 square micrometers and not more than 19.625 square micrometers.

* * * * *